US011359044B2

(12) United States Patent
Yin et al.

(10) Patent No.: US 11,359,044 B2

(45) Date of Patent: Jun. 14, 2022

(54) PREPARATION AND APPLICATION OF NOVEL MULTIFUNCTIONAL NANOCOMPOSITE MATERIAL WITH NEW PHOTOSENSITIZER

(71) Applicant: Jiangnan University, Wuxi (CN)

(72) Inventors: Jian Yin, Wuxi (CN); Jing Hu, Wuxi (CN); Zhou Ye, Wuxi (CN); Yijian Rao, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 524 days.

(21) Appl. No.: 16/374,910

(22) Filed: Apr. 4, 2019

(65) Prior Publication Data

US 2019/0224318 A1 Jul. 25, 2019

Related U.S. Application Data

(63) Continuation of application No. PCT/CN2018/082674, filed on Apr. 11, 2018.

(30) Foreign Application Priority Data

Jan. 15, 2018 (CN) ........................ 201810033885.3

(51) Int. Cl.

| | |
|---|---|
| ***A61K 41/00*** | (2020.01) |
| ***C08F 220/36*** | (2006.01) |
| ***A61K 49/00*** | (2006.01) |
| ***A61P 35/00*** | (2006.01) |
| ***A61K 9/107*** | (2006.01) |
| ***A61K 47/32*** | (2006.01) |
| ***A61K 31/357*** | (2006.01) |
| ***C08F 2/50*** | (2006.01) |
| *C08F 220/34* | (2006.01) |

(52) U.S. Cl.

CPC .......... *C08F 220/36* (2013.01); *A61K 9/1075* (2013.01); *A61K 31/357* (2013.01); *A61K 41/0057* (2013.01); *A61K 47/32* (2013.01); *A61K 49/0054* (2013.01); *A61K 49/0078* (2013.01); *A61P 35/00* (2018.01); *C08F 2/50* (2013.01); *C08F 220/34* (2013.01)

(58) Field of Classification Search

CPC .... A61K 47/32; A61K 47/58; A61K 49/0041; C08F 220/34

See application file for complete search history.

(56) References Cited

U.S. PATENT DOCUMENTS

| | | | | |
|---|---|---|---|---|
| 2002/0143066 A1* | 10/2002 | Miller | ..................... | A61P 31/04<br>514/656 |
| 2016/0331839 A1* | 11/2016 | Vanbever | ........... | A61K 38/1709 |

FOREIGN PATENT DOCUMENTS

| | | | |
|---|---|---|---|
| CN | 1531442 A | | 9/2004 |
| CN | 103289099 A | | 9/2013 |
| CN | 105412924 A | | 3/2016 |
| CN | 105646892 A | * | 6/2016 |
| CN | 105646892 A | | 6/2016 |
| CN | 105999282 A | | 10/2016 |

OTHER PUBLICATIONS

Sonoke et al, "Galactose-Modified Cationic Liposomes as a Liver-Targeting Delivery System for Small Interfering RNA", Biol. Pharm. Bull. 34(8) 1338-1342 (2011) (Year: 2011).*

* cited by examiner

*Primary Examiner* — James W Rogers

(74) *Attorney, Agent, or Firm* — IPro, PLLC

(57) ABSTRACT

The present disclosure discloses preparation and application of a novel multifunctional nanocomposite material with new photosensitizer, and belongs to the technical field of photodynamic therapy and the field of biomedicine. The photosensitizer multifunctional nanocomposite material provided by the present disclosure is prepared by self-assembly of cercosporin and an acid-sensitive copolymer multifunctional material with liver tumor cell targeting ability and traceability, wherein the acid-sensitive copolymer multifunctional material can be a copolymer of poly(N,N-dimethylaminoethyl methacrylate) and poly-3-azido-2-hydroxypropyl methacrylate covalently linked by galactose-modified rhodamine B. The photosensitizer multifunctional nanocomposite material disclosed by the present disclosure can specifically recognize liver tumor cells and be endocytosed into the cells through galactose-asialoglycoprotein receptor interaction, and can trigger the release of the photosensitizer cercosporin under acidic pH conditions to exert photodynamic therapy efficiency. The novel photosensitizer multifunctional nanocomposite material has a good application prospect in targeted photodynamic therapy of tumor cells.

12 Claims, 6 Drawing Sheets

PREPARATION AND APPLICATION OF NOVEL MULTIFUNCTIONAL NANOCOMPOSITE MATERIAL WITH NEW PHOTOSENSITIZER

TECHNICAL FIELD

The disclosure herein relates to preparation and application of a novel multifunctional nanocomposite material with new photosensitizer, specifically relates to cercosporin which is further coated into an acid-sensitive copolymer with liver tumor cell targeting ability and traceability to prepare the novel photosensitizer multifunctional nanocomposite material, and a preparation method and application thereof, belonging to the technical field of photodynamic therapy and the field of biomedicine.

BACKGROUND

Photodynamic therapy is a non-invasive new technology for treatment of tumor diseases. By incubating a photosensitizer and combining with specific light irradiation, singlet oxygen with high oxidizability can be produced, thereby achieving the purpose of killing tumor tissues and cells. After years of development, photodynamic therapy has become more and more widely used, and its mechanism of action has become increasingly clear. Photodynamic therapy for treatment of malignant tumors requires three elements: photosensitizer, light irradiation with specific wavelength and oxygen. The treatment strategy is as follows: a low-toxic photosensitizer enters the body; then light is applied to a tumor area to excite the photosensitizer; the photosensitizer in an excited triplet state after photoactivation transfers the excited state energy to the oxygen in the surrounding tumor tissues and cells to produce singlet oxygen with high oxidizability, thereby oxidatively damaging liposomes, proteins and other subcellular organelles, and further causing tumor cell apoptosis and necrosis. Therefore, the performance of the photosensitizer to produce singlet oxygen is critical to the effect of photodynamic therapy. However, the photosensitizer commonly used has poor water-solubility and does not have tumor targeting ability, which severely restricts its clinical application. Therefore, many scientific studies have enhanced the water solubility and targeting ability of various photosensitizers by means of chemical modification or nano-delivery systems to meet the application of the photodynamic therapy technology in the field of biomedicine.

After decades of development, the types and performance of photosensitizers have been fully developed, and the photosensitizers have developed to the third generation: the first and second generation photosensitizers are mainly classified into porphyrin derivatives, meso-aryl-substituted porphins, phthalocyanines, chlorophyll a degradation product derivatives and hematoporphyrin monomethyl ether; the third-generation photosensitizers mainly refer to functionalized derivatives of the second-generation photosensitizers, including amino acid-coupled photosensitizers, polymer-coupled photosensitizers, protein or sugar-coupled photosensitizers, and other photosensitizers with molecular recognition function. The development of each generation of photosensitizers is accompanied by improvements in its phototherapy performance, particularly in terms of hydrophilicity and targeting ability. At present, in medical application of photodynamic therapy, the comparatively mature photosensitizers include porphyrins, porphins and phthalocyanines. In addition, a novel photosensitive material, cercosporin, is a perylenequinonoid-based photosensitive compound isolated from the genus *Cercospora*, and has high singlet oxygen quantum yield (0.81). However, similar to other photosensitizers, cercosporin has poor water-solubility and lacks targeting ability, its photodynamic therapy function has not yet been developed, and currently, there is no report on its use as a photosensitizer in photodynamic therapy.

Polymer micelles are a kind of nano-delivery systems, and amphiphilic macromolecules with good biocompatibility can self-assemble into micelles in water. The hydrophobic photosensitizer can be constructed into a photosensitizer-loaded micelle in the form of drug-loading or performing hydrophilic modification to meet the requirements of photodynamic therapy. In addition, due to special growth properties of tumor tissues or cells, multiple targeting receptors can be overexpressed on the surface of cell membranes; while some functional targeting molecules, such as antibodies, peptides, carbohydrates, etc., can specifically recognize these receptors, and thus can be modified on the surface of the polymer micelles, so the polymer micelles can be ingested by tumor cells in a large amount through receptor-mediated recognition, thereby achieving targeted delivery of the photosensitizer for photodynamic therapy, and reducing the toxicity of photodynamic therapy to normal cells.

SUMMARY

In order to solve the shortcomings of low water solubility and lack of targeting ability of photosensitizers in photodynamic therapy and develop the potential of cercosporin in photodynamic therapy, the present disclosure applies cercosporin to multifunctional nanocomposite materials for the first time, thereby reducing its toxic and side effects and developing its potential in photodynamic therapy.

The novel multifunctional nanocomposite material with new photosensitizer provided by the present disclosure is prepared by self-assembly of cercosporin and an acid-sensitive copolymer multifunctional delivery system with liver tumor cell targeting ability and traceability, and is capable of forming stable nanostructures and triggering explosive release of cercosporin under acidic conditions. Targeted delivery of cercosporin for photodynamic therapy is achieved, which improves the toxicity of cercosporin to hepatoma cells and reduces the toxicity of cercosporin to normal cells. The acid-sensitive copolymer multifunctional delivery system can be a copolymer of poly(N,N-dimethylaminoethyl methacrylate) and poly-3-azido-2-hydroxypropyl methacrylate covalently linked by galactose-modified rhodamine B.

One aspect of the present disclosure relates to an acid-sensitive copolymer multifunctional delivery system with liver tumor cell targeting ability and traceability, which is a compound represented by the following formula 1:

Formula 1

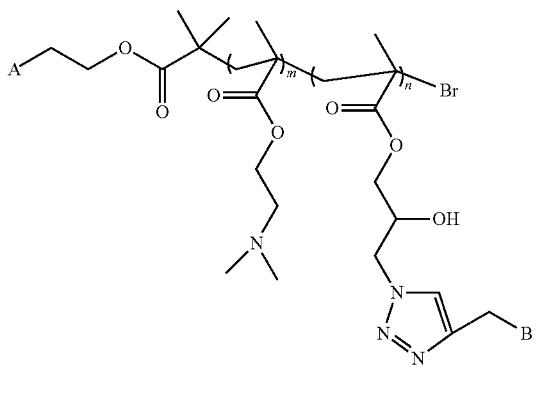

In formula 1,

A is one or more identical or different fluorescent molecules having the fluorescent tracing function selected from rhodamine B, fluorescein isothiocyanate, fluoroboron dipyrrole, etc.;

B is one or more identical or different monosaccharide or oligosaccharide molecules having galactose or galactosamine residues, which are capable of specifically recognizing over-expressed asialoglycoprotein receptors on the surface of hepatoma cells;

formula 1 contains the monomer structure of N,N-dimethylaminoethyl methacrylate (DMAEMA), and m represents the degree of polymerization and is equal to 42;

formula 1 contains the monomer structure of 3-azido-2-hydroxypropyl methacrylate (GMA-$N_3$), and n represents the degree of polymerization and is equal to 62.

In one embodiment of the present disclosure, the acid-sensitive copolymer multifunctional delivery system with liver tumor cell targeting ability and traceability is represented by formula 1, wherein the molar ratio of the fluorescent molecule rhodamine B to DMAEMA to GMA-$N_3$ is 1:42:62, and the molar ratio of the targeting sugar molecule to GMA-$N_3$ is 1:1.

A method for preparing an acid-sensitive copolymer multifunctional delivery system with liver tumor cell targeting ability and traceability, comprising the following steps: modifying a fluorescent molecule with a fluorescent imaging function into a macroinitiator, and triggering free radical polymerization between the monomer 3-azido-2-hydroxypropyl methacrylate (GMA-$N_3$) and N,N-dimethylaminoethyl methacrylate (DMAEMA), thereby forming a polymer covalently bonded with the fluorescent molecule, wherein PGMA-$N_3$ in the polymer has a function of loading a hydrophobic drug through hydrophilic-hydrophobic interaction, and the PDMAEMA moiety can coat a nucleic acid substance due to its large amount of amino groups, and is protonated under acidic conditions, thereby triggering a sponge effect to cause the inclusion bodies to escape; the galactose-terminated position having a liver-targeting function is modified to contain an alkynyl group and can be covalently bonded to the copolymer by a click reaction with an azide group of the PGMA-$N_3$ moiety in the copolymer, thereby providing a stable targeting function for a vector.

The method further comprises:

adding bromo-rhodamine B initiator, monomer DMAEMA and monomer GMA-$N_3$ into a 25 mL round bottom flask according to a molar ratio of 1:25:50, dissolving with 2 mL of tetrahydrofuran, and introducing argon gas for 30 minutes to remove oxygen from the flask, wherein a stabilizer needs to be removed from the monomer DMAEMA in advance, that is, enabling crude DMAEMA to quickly pass through a basic alumina column; under a nitrogen protection condition, successively adding copper bromide and pentamethyldiethylenetriamine, sealing the flask and reacting at room temperature for 8 hours under the nitrogen protection condition; after the reaction is completed, adding tetrahydrofuran (10 mL) into the reaction solution, thoroughly stirring for dissolving the reaction solution in the flask, and passing through a neutral alumina column to remove the copper ligand from the mixed solution; collecting the obtained liquid and removing the solvent by rotary evaporation, slowly dropwise adding the viscous liquid in the flask to petroleum ether (500 mL) to perform precipitating repeatedly for three times, and vacuum drying the obtained precipitate to obtain a rhodamine B-modified copolymer.

Dissolving propargyl modified deacetyl galactose and the rhodamine B modified copolymer in 5 mL of DMF, then dissolving copper sulfate and sodium ascorbate in 5 mL of water and then dropwise adding to the above reaction solution, and stirring the reaction solution at room temperature for 48 hours. Filtering the reaction solution, and dialyzing in an aqueous solution (molecular weight cutoff of a dialysis bag: 8-10 kDa) to obtain a target copolymer Gal-polymer.

A method for preparing a cercosporin-coated multifunctional nanocomposite material, comprising the following steps:

1) respectively dissolving a target copolymer Gal-polymer and cercosporin with DMSO, and mixing and stirring the two solutions for 6 hours;

2) dialyzing the mixed solution in double distilled water for 48 hours, and changing water once every 12 hours to prepare a photosensitizer multifunctional nanocomposite material solution;

3) filtering the photosensitizer multifunctional nanocomposite material solution with a 0.45 μm micromembrane to remove unloaded cercosporin, and performing freeze drying by using a freeze drier to obtain a photosensitizer multifunctional nanocomposite material Cer@Gal-polymer.

A GMA monomer in the acid-sensitive nano-polymer multifunctional delivery system with liver tumor cell targeting ability and traceability according to the present disclosure is used for providing a hydrophobic portion, on the one hand, the GMA monomer interacts with hydrophobic cercosporin to coat the cercosporin in its water delivery core, and on the other hand, the —$N_3$ group of the GMA monomer can chemically react with propargyl-containing galactose to covalently bond and introduce a targeted galactose molecule to the polymer; the DMAEMA monomer is to provide a hydrophilic portion on the one hand, on the other hand, because it contains a large amount of amino groups, it can be protonated under acidic conditions to cause micelle dissociation to release the coated photosensitizer, and it can escape from the endoplasmic reticulum of the cell by triggering a sponge effect, thereby releasing the coated photosensitizer into the cytoplasm or even the nucleus.

The novel photosensitizer multifunctional nanocomposite material according to the present disclosure has the following beneficial effects:

(1) The photosensitizer multifunctional nanocomposite material Cer@Gal-polymer of the present disclosure can stably exist during a transportation process (pH 7.4), photosensitizer leakage can be effectively reduced, and the efficiency of producing singlet oxygen under light irradiation conditions is significantly reduced; while in an acidic pH environment, photosensitizer release is accelerated, the photosensitizer release amount is increased, and a large amount of singlet oxygen is produced so as to produce cytotoxicity.

(2) The photosensitizer multifunctional nanocomposite material Cer@Gal-polymer of the present disclosure can promote real-time imaging in vitro and in vivo because it contains covalently bonded rhodamine B molecules.

(3) The photosensitizer multifunctional nanocomposite material Cer@Gal-polymer of the present disclosure can target over-expressed asialoglycoprotein receptors on the surface of hepatoma cells because it contains covalently linked galactose molecules, thereby realizing targeted delivery.

(4) After being endocytosed into cells via specific recognition of galactose-asialoglycoprotein receptors, the photosensitizer multifunctional nanocomposite material Cer@Gal-polymer of the present disclosure can successfully escape from acidic organelles into cytoplasm or even the nucleus to play the role of the photosensitizer.

DETAILED DESCRIPTION

Figure 1:
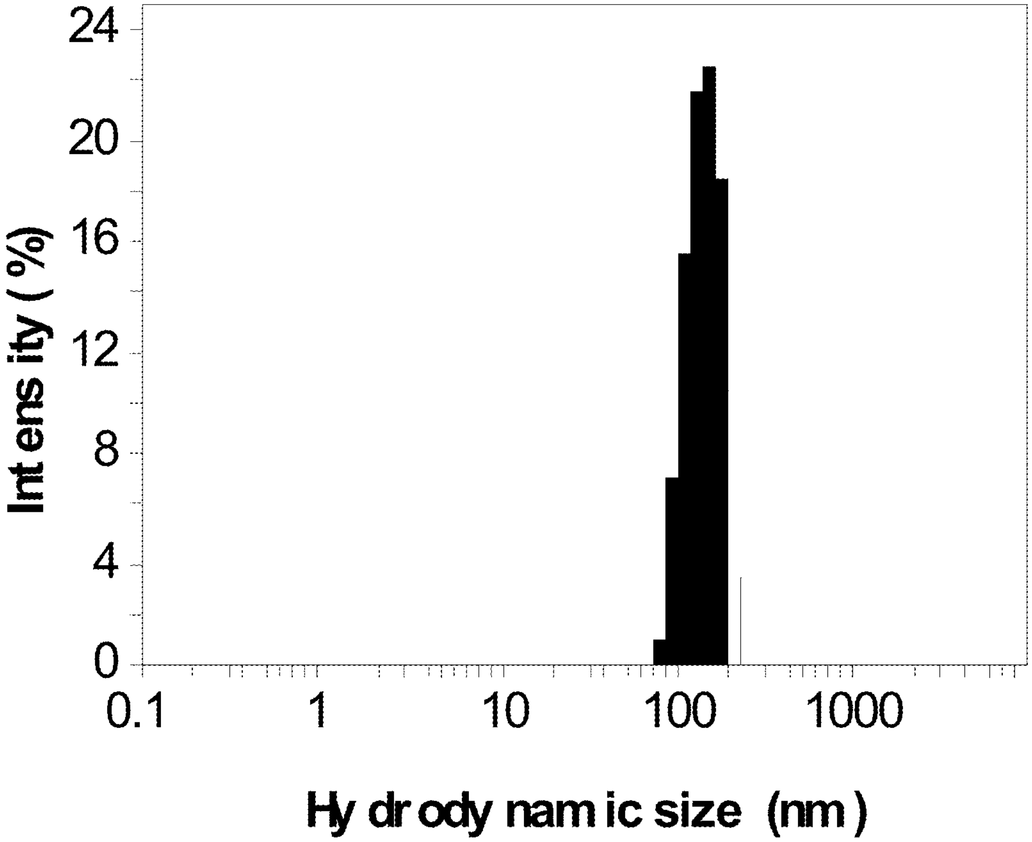
FIG. 1 is a dynamic light scattering particle size distribution diagram of photosensitizer multifunctional nanocomposite material Cer@Gal-polymer.

Embodiment plan of the present disclosure will be described in detail below with reference to the examples, but those skilled in the art will understand that the following examples are intended to illustrate the present disclosure and are not to be considered as limiting the scope of the present disclosure. If no specific conditions are specified in the examples, operations are carried out according to the general conditions or the conditions recommended by manufacturers. Any reagents or instruments that are not indicated with the manufacturers are commercially available products.

Example 1

Preparation of a Bromo-Rhodamine B Initiator

Weighing and putting 15.52 g (25.00 mmol) of ethylene glycol and 1.01 g (10.00 mmol) of triethylamine in a 100 mL erlenmeyer flask and stirring, cooling to 0° C. in an ice water bath, dropwise adding 1.20 mL (10.00 mmol) of 2-bromoisobutyryl bromide under a nitrogen atmosphere, then slowly raising the temperature to room temperature and magnetically stirring for 3 hours. Adding 100 mL of deionized water to the reacted solution for quenching and extracting with dichloromethane (100 mL×3). Extracting the collected organic phase with deionized water (100 mL×3). Adding an appropriate amount of anhydrous magnesium sulfate to the organic phase obtained by extraction, and drying for 12 hours. After filtration, performing rotary evaporation to obtain a crude oily product, and performing distillation under reduced pressure (85° C., 30 mTorr) to obtain a colorless viscous product 2-hydroxyethyl 2-bromoisobutyrate.

Dissolving 4.81 g (10.00 mmol) of rhodamine B, 2.90 g (15.00 mmol) of 1-ethyl-(3-dimethylaminopropyl) carbodiimide hydrochloride and 3.22 g (15.00 mmol) of a compound 2-hydroxyethyl 2-bromoisobutyrate in 40 mL of anhydrous dichloromethane and stirring, cooling to 0° C. in an ice water bath, adding 1.82 g of 4-dimethylaminopyridine (15 μmop, then, slowly raising the temperature to room temperature and reacting for 12 hours. Extracting the reaction solution with 0.1 M of HCl (50 mL×3), then respectively washing with a saturated sodium hydrogen carbonate solution and a saturated saline solution for three times, drying and filtering the organic phase with anhydrous magnesium sulfate, removing the solvent by rotary evaporation, and performing separation with a silica gel column (dichloromethane/methanol=10:1) to obtain the bromo-rhodamine B initiator. Specific methods can be found in the reference (Marcromolecules, 2011, 44, 2050-2057).

Example 2

Preparation of 3-azido-2-hydroxypropyl Methacrylate GMA-$N_3$

Dissolving 3.71 g (57.00 mmol) of sodium azide and 3.81 g (45.20 mmol) of sodium hydrogen carbonate in 60 mL of tetrahydrofuran/water (5:1 v $v^{-1}$) and stirring, slowly adding 5.42 g (37.80 mmol) of glycidyl methacrylate, and reacting at room temperature for 48 hours. Filtering to remove insoluble salt substances, removing the solvent by rotary evaporation, extracting the obtained concentrate twice with dichloromethane, drying and filtering the obtained organic phase with anhydrous magnesium sulfate, removing the solvent by rotary evaporation, and performing separation with a silica gel column (hexane/ethyl acetate=9:1) to obtain 3-azido-2-hydroxypropyl methacrylate. Specific methods can be found in the references (Polymer Chemistry, 2015, 6, 3875-3884; Soft Matter, 2009, 5, 4788-4796).

Example 3: Preparation of Copolymer of poly(N,N-dimethylaminoethyl methacrylate) and poly-3-azido-2-hydroxypropyl Methacrylate Covalently Linked by Rhodamine B (RhB-PDMAEMA42-c-PGMA62-$N_3$)

Accurately weighing 70.0 mg (0.10 mmol) of bromo-rhodamine B initiator, 484.0 mg (2.75 mmol) of monomer DMAEMA and 1.01 g (5.50 mmol) of compound 3-azido-2-hydroxypropyl methacrylate, adding to a 25 mL round bottom flask, dissolving with 2 mL of tetrahydrofuran, and introducing argon gas for 30 minutes to remove oxygen from the flask, wherein the stabilizer in the monomer DMAEMA needs to be removed in advance, that is, enabling crude DMAEMA to quickly pass through a basic alumina column; under a nitrogen protection condition, successively adding 18.9 mg (0.10 mmol) of CuBr and PMDETA (28 μL, 0.10 mmol), sealing the flask and reacting at room temperature for 8 hours under the nitrogen protection condition. After the reaction is completed, adding tetrahydrofuran (10 mL) to the reaction solution, thoroughly stirring the reaction solution in the flask, and passing through a neutral alumina column to remove the copper ligand from the mixed solution; collecting the obtained liquid and removing the solvent by rotary evaporation, slowly dropwise adding the viscous liquid in the flask to petroleum ether (500 mL) to perform precipitating repeatedly for three times, and vacuum drying the obtained precipitate to obtain the rhodamine B-modified copolymer RhB-PDMAEMA42-c-PGMA62-$N_3$.

Example 4

Preparation of Propargyl-Modified Deacetyl Galactose

Dissolving 6.21 g (15.90 mmol) of peracetyl galactose in 75 mL of anhydrous dichloromethane, adding 1.0 mL (18.00 mmol) of propargyl alcohol, cooling to 0° C. and stirring for 5 minutes, and dropwise adding 3.0 mL (24.30 mmol) of boron trifluoride etherate within 15 minutes. After continuing stirring at 0° C. for 10 minutes, reacting at room temperature for 10 hours. Stopping the reaction with a saturated potassium carbonate solution, extracting the organic phase with dichloromethane, washing the organic phase with a saturated saline solution for three times, drying and filtering the organic phase with anhydrous magnesium sulfate, and removing the solvent by rotary evaporation to obtain the propargyl-modified peracetyl galactose.

Dissolving 2.01 g (5.20 mmol) of propargyl-modified peracetyl galactose in 50 mL of 0.30 mol $L^{-1}$ sodium methoxide methanol solution and reacting at room temperature. Testing the plate until the disappearance of the starting materials, adjusting the reaction solution to neutral by adding $H^+$ exchange resin, performing filtering, removing the solvent by rotary evaporation, and performing separation with a silica gel column (dichloromethane/methanol=10:1) to obtain the propargyl-modified deacetyl galactose. Specific methods can be found in the reference (Bioconjugate Chemistry, 2012, 23, 1166-1173).

Example 5

Preparation of Copolymer of poly(N,N-dimethylaminoethyl methacrylate) and poly-3-azido-2-hydroxypropyl Methacrylate Covalently Linked by Galactose-Modified Rhodamine B (Gal-Polymer)

Dissolving 350.0 mg of the propargyl-modified deacetyl galactose of Example 4 and 200.1 mg of the rhodamine B-modified copolymer RhB-PDMAEMA25-c-PGMA50-$N_3$ of Example 3 in 5 mL of DMF, then, dissolving 98.0 mg (0.61 mmol) of copper sulfate and 242.0 mg (1.2 mmol) of sodium ascorbate in 5 mL of water, dropwise adding into the above reaction solution, and stirring the reaction solution at room temperature for 48 hours. Filtering the reaction solution, and dialyzing in an aqueous solution (molecular weight cutoff of a dialysis bag: 8-10 kDa) to obtain a target copolymer Gal-polymer.

Example 6

Preparation of Novel Photosensitizer Multifunctional Nanocomposite Material (Cer@Gal-Polymer)

Respectively dissolving the copolymer Gal-polymer of Example 5 and cercosporin in DMSO, and mixing and stirring the two solutions for 6 hours. Dialyzing the mixed solution in double distilled water for 48 hours, and changing water once every 12 hours to prepare a cercosporin-loaded photosensitizer multifunctional nanocomposite material solution; then filtering the photosensitizer multifunctional nanocomposite material solution with a 0.45 μm micromembrane to remove unloaded cercosporin, and performing freeze drying by using a freeze drier to obtain a cercosporin-coated photosensitizer multifunctional nanocomposite material Cer@Gal-polymer.

Fully dissolving the prepared photosensitizer multifunctional nanocomposite material in DMSO, and measuring the absorbance of the solution at 463 nm by a microplate reader. The concentration of cercosporin in the composite nanomaterial can be obtained according to the calibration curve prepared by the cercosporin DMSO solution. The loading amount of cercosporin in the obtained photosensitizer multifunctional nanocomposite material=the mass of the cercosporin in the composite material/the mass of the copolymer, which is 9.0%; the encapsulation ratio=the mass of the cercosporin in the composite/the mass of the starting cercosporin, which is 35.6%.

Example 7

Characterization of Novel Photosensitizer Multifunctional Nanocomposite Material (Cer@Gal-Polymer)

Figure 2:
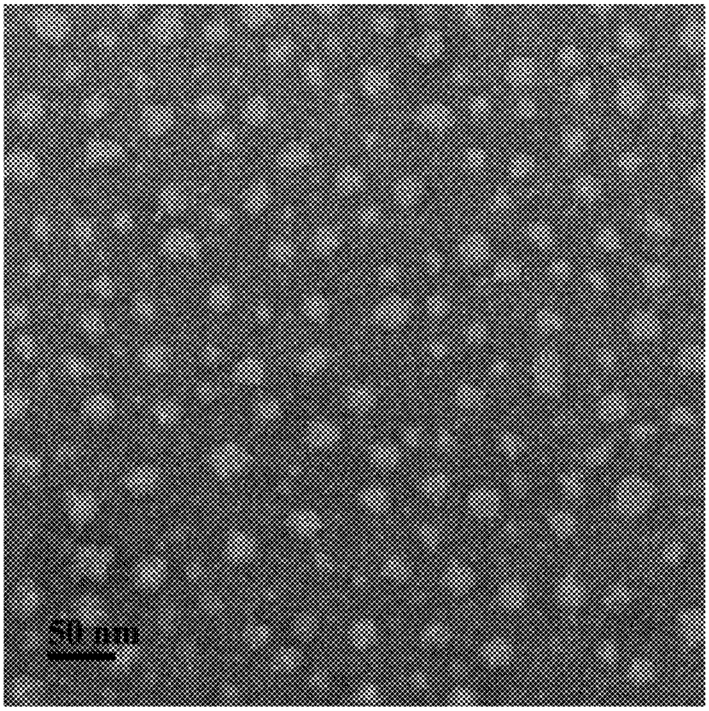
FIG. 2 is a transmission electron micrograph of photosensitizer multifunctional nanocomposite material Cer@Gal-polymer.

Measuring the particle size distribution of the Cer@Gal-polymer prepared in Example 6 by dynamic light scattering technique, and observing its morphological features by a transmission electron microscope. As shown in FIG. 1, Cer@Gal-polymer can form micelles with a particle size of about 103±9.9 nm by dynamic light scattering particle size detection. As shown in FIG. 2, it exhibits a circular structure, and has uniform particle size distribution observed by the transmission electron microscope.

Figure 3:
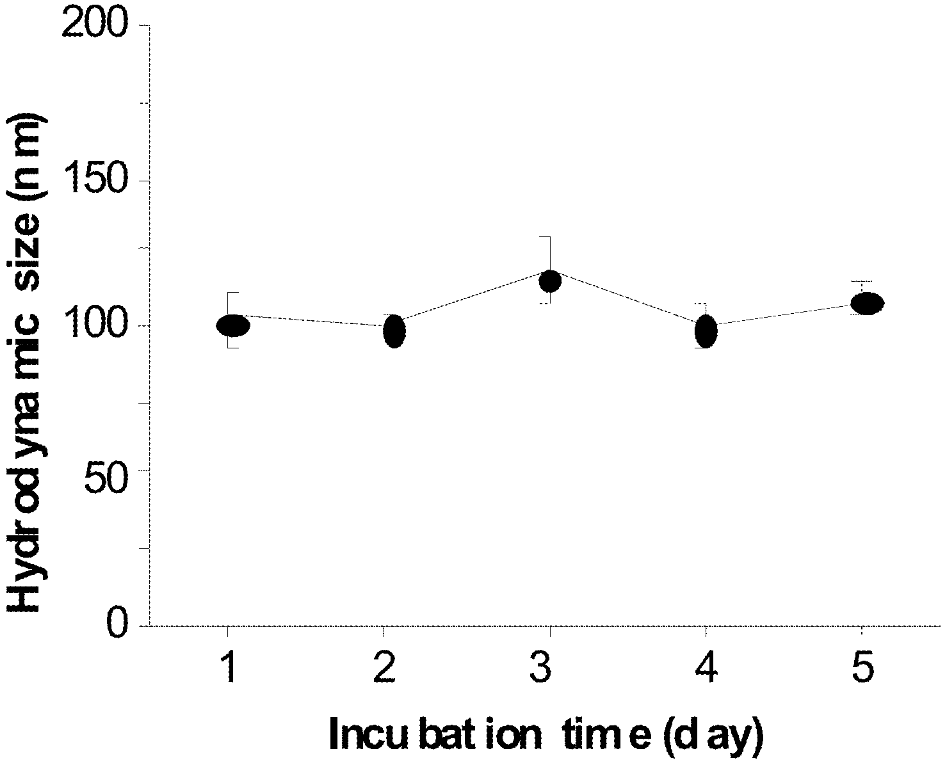
FIG. 3 is a particle size change diagram of photosensitizer multifunctional nanocomposite material Cer@Gal-polymer incubated for 5 days in high-sugar medium containing 10% fetal bovine serum.

Stability is one of the most important properties of a photosensitizer multifunctional nanocomposite material. Nanoparticles used in biomedical fields must be stably dispersed in a medium. The photosensitizer multifunctional nanocomposite material Cer@Gal-polymer prepared in this experiment is dispersed in a medium containing 10% fetal bovine serum to determine the particle size change. As shown in FIG. 3, there is no significant particle size change within 5 days, which indicates that the photosensitizer multifunctional nanocomposite material has good stability.

Example 8

Acid-Sensitive Release Characteristics of Novel Photosensitizer Multifunctional Nanocomposite Material (Cer@Gal-Polymer)

Respectively dissolving 12 mg of Cer@Gal-polymer prepared in Example 6 in 1 mL of PBS of pH 5.0 or pH 7.4, filling in dialysis bags (MWCO 2000 Da), and respectively placing the sealed dialysis bags in beakers containing 35 mL of a PBS buffer solution of pH 5.0 or pH 7.4 (each containing 1% Tween 20). Placing the beakers on a constant temperature (37° C.) magnetic stirrer, setting the sampling time, taking 200 μL of the release solutions from the beakers by using a pipette, and replenishing 200 μL of fresh buffer solutions of the corresponding pH values. Measuring the absorption intensity of cercosporin in the release solutions by a microplate reader, and calculating the cumulative release amount.

Figure 4:
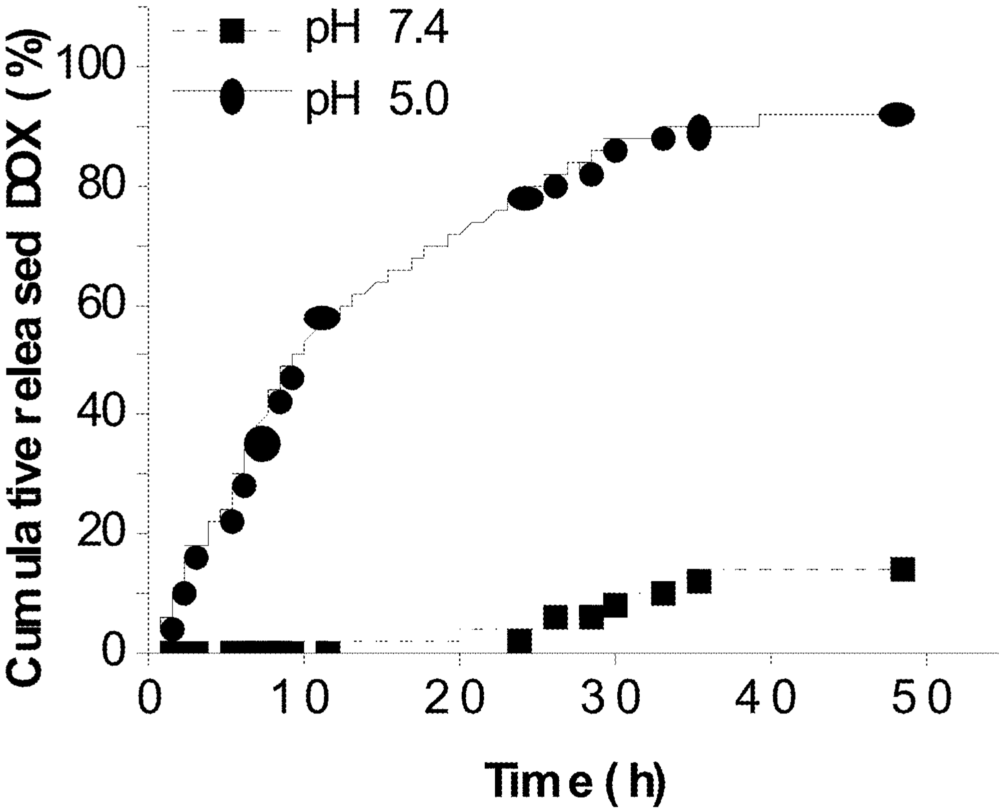
FIG. 4 is cercosporin release rate of photosensitizer multifunctional nanocomposite material Cer@Gal-polymer in PBS of pH 7.4 and 5.0.

As shown in the results in FIG. 4, it is found that in a neutral medium, the release of cercosporin is slow, and the release rate is only 15% after 48 hours; while in an acidic medium, cercosporin exhibits a "burst release" phenomenon, with a cumulative release amount of 78% within 24 hours, and a cumulative release amount of 93% after 48 hours. Such release results indicate that the novel photosensitizer multifunctional nanocomposite material (Cer@Gal-polymer) can stably exist under neutral physiological conditions, so the toxic and side effects on normal tissues are reduced; while in the acidic environment of tumor cells, cercosporin can be quickly released for subsequent photodynamic therapy.

Example 9

Determination of Singlet Oxygen Production Capacity of Photosensitizer Cercosporin The singlet oxygen production capacity of a photosensitizer is an important indicator for evaluating its application in photodynamic therapy. To evaluate the singlet oxygen production capacity of the photosensitizer cercosporin, the intensity change of the characteristic absorption peak of a singlet oxygen trapping agent 1,3-diphenylisobenzofuran (DPBF) is adopted to characterize the generation of singlet oxygen.

Figure 5:
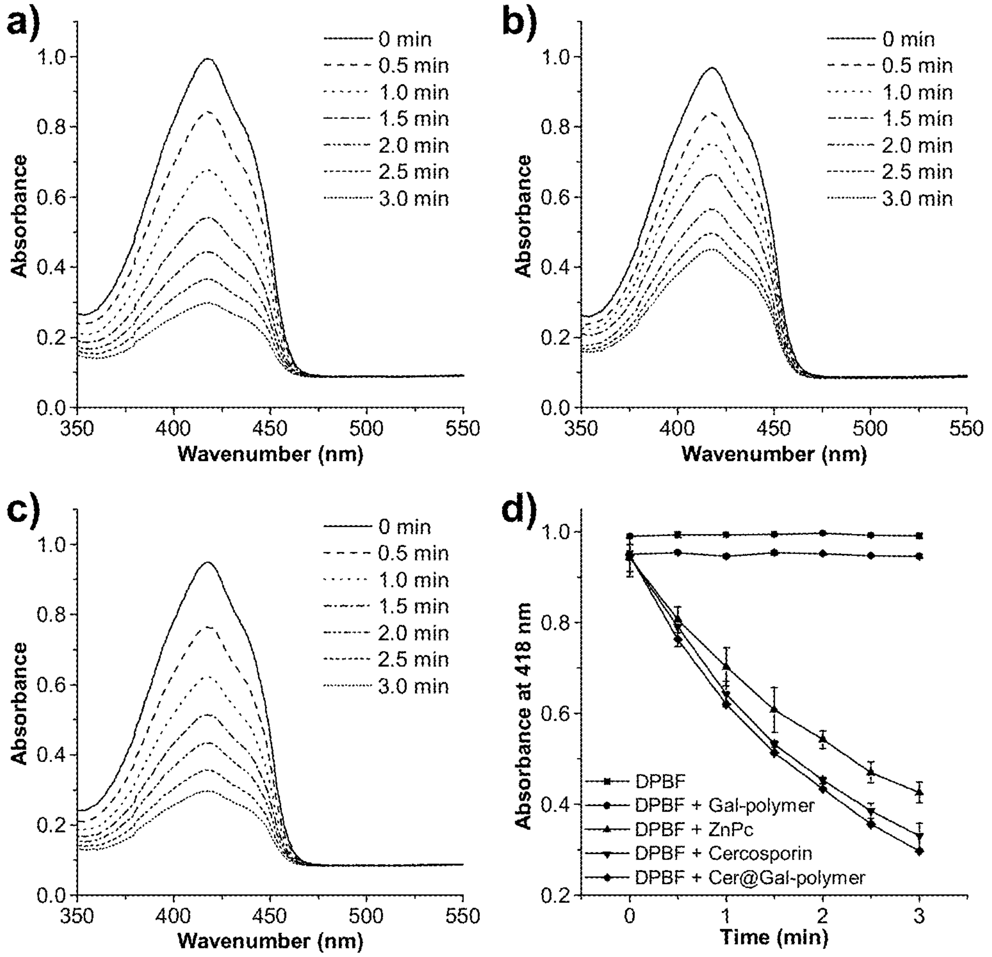
FIG. 5 is absorbance spectra (350-550 nm) of 1,3-diphenylisobenzofuran (DPBF) under different treatments. a) Cercosporin dissolved in DMSO; b) zinc phthalocyanine dissolved in DMSO; c) photosensitizer multifunctional nanocomposite material Cer@Gal-polymer dissolved in DMSO; d) changes in absorbed light intensity of the above three solutions at 418 nm.

As shown in FIG. 5, the singlet oxygen yield of zinc phthalocyanine ZnPc in DMSO is 0.67 and is used as a control. Adding a DMSO solution (1.5 μL, 0.1 mM) of cercosporin, Cer@Gal-polymer or ZnPc to 3 mL of a DPBF solution, and measuring the absorbance spectra (350-550 nm) after 0.5, 1.0, 1.5, 2.0, 2.5 and 3.0 minutes of irradiation at 463 nm. According to a formula $\Phi_{\Delta(cercosporin)}=\Phi_{\Delta(ZnPc)}\times[S_{(cercosporin)}/S_{(ZnPc)}]\times[1\text{-}10^{-OD(ZnPc)}]/[1\text{-}10^{-OD(cercosporin)}]$, the singlet oxygen quantum yield of the cercosporin is calculated to be 0.83, where $\Phi_\Delta$ represents the singlet oxygen quantum yield, $S_{(cercosporin)}$ represents the DPBF consumption rate of cercosporin, $S_{(ZnPc)}$ represents the DPBF consumption rate of a reference solution, $OD_{(ZnPc)}$ represents the absorbance of ZnPc at 463 nm, and $OD_{(cercosporin)}$ represents the absorbance of cercosporin at 463 nm. The measured singlet oxygen quantum yield of cercosporin in Cer@Gal-polymer is 0.87, which is slightly higher than that of cercosporin alone. The reason is that rhodamine B in the polymer material also absorbs the light intensity and then transfers the energy of the emission wavelength to cercosporin to re-excite the production of singlet oxygen.

Example 10

Determination of Singlet Oxygen Production Capacity of Novel Photosensitizer Multifunctional Nanocomposite Material (Cer@Gal-polymer) Under Different pH Conditions 9,10-anthryl-bis(methylene)dimalonic acid (ABDA) can be used as an agent for measuring singlet oxygen production in an aqueous solution. When the novel photosensitizer multifunctional nanocomposite material (Cer@Gal-polymer) is under the irradiation of light of a specific wavelength, ABDA can be oxidized by the produced singlet oxygen, thereby enabling its fluorescence intensity to be reduced, and further indirectly characterizing the formation of singlet oxygen of the Cer@Gal-polymer. Respectively adding 150 μL of Cer@Gal-polymer (1 mg $mL^{-1}$ in PBS of pH 5.0) and 150 μL of Cer@Gal-polymer (1 mg $mL^{-1}$ in PBS of pH 7.4) to 2 mL of ABDA (13 mM in PBS of pH 5.0 or PBS of pH 7.4), and measuring the fluorescence spectra (400-550 nm) after 10, 20, 30, 40 and 50 seconds of irradiation at 463 nm.

Figure 6:
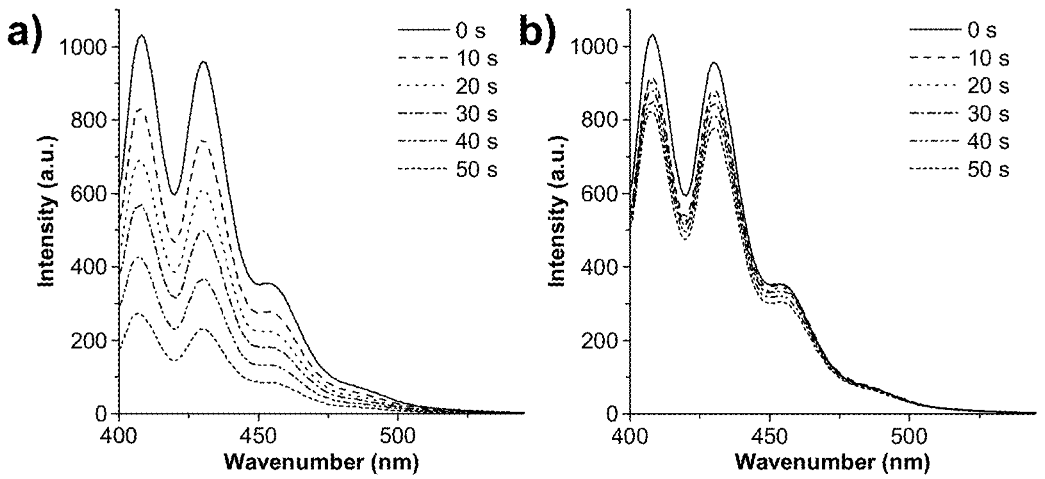
FIG. 6 is fluorescence spectra (400-550 nm) of 9,10-anthryl-bis(methylene)dimalonic acid (ABDA) under different treatments. a) Photosensitizer multifunctional nanocomposite material Cer@Gal-polymer dissolved in PBS of pH 5.0; b) photosensitizer multifunctional nanocomposite material Cer@Gal-polymer dissolved in PBS of pH 7.4.

As shown by the results in FIG. 6, when the pH of the system is 7.4, the fluorescence intensity of ABDA does not change much, that is, singlet oxygen production is hardly detected; but when the pH of the system is 5.0, the fluorescence intensity of ABDA is obviously weakened with the increase of irradiation time, indicating that a large amount of singlet oxygen is produced. This result indicates that under acidic conditions, cercosporin can be released from the nanocomposite to exert photodynamic therapy efficiency, while in a normal body fluid environment, it is coated in the nanocomposite and does not exhibit its photodynamic performance.

Example 11

Demonstration of Ability of Photosensitizer Multifunctional Nanocomposite Material Cer@Gal-polymer to Specifically Target and Recognize Asialoglycoprotein Receptors on Surface of Hepatoma Cells HepG2 by Flow Cytometry In the flow cytometry test, culturing HepG2 and HEK293 cells in DMEM media (containing 100 U/mL penicillin and 100 μg/mL streptomycin) containing 10% newborn bovine serum, and placing in a 37° C. incubator containing 5% $CO_2$ for growth. Taking the cells in the logarithmic growth phase, after digesting with 0.02% EDTA and 0.25% trypsin digestion fluid, inoculating the cells in 6-well plates according to $5\times10^4$ cells per well, adding 2 mL of a complete culture solution to each well, placing the culture plate in an incubator and culturing for 24 hours. Adding galactose with a final concentration of 10 mmol $L^{-1}$ to one group of HepG2 cells, after continuing culturing for 24 hours, when the cell density of each group reaches 70%, continuing culturing for 8 hours by adding Cer@Gal-polymer. Digesting the cells with trypsin, centrifuging at 1000 rpm for 3 minutes, discarding the supernatant, and resuspending and dispersing the cumulative cells in PBS. Repeating the centrifugation process for three times to remove residual media and micelle solutions and reduce interference to fluorescence detection. Finally, dispersing the cells in PBS, placing in a flow tube, and measuring the fluorescence intensity of each group of cells by flow cytometry.

In the experiment, HepG2 cells are cultured by two ways, respectively in a medium containing galactose (the surface receptor is saturated with galactose in advance) and in a medium containing no galactose (the surface asialoglycoprotein receptor is not affected).

Figure 7:
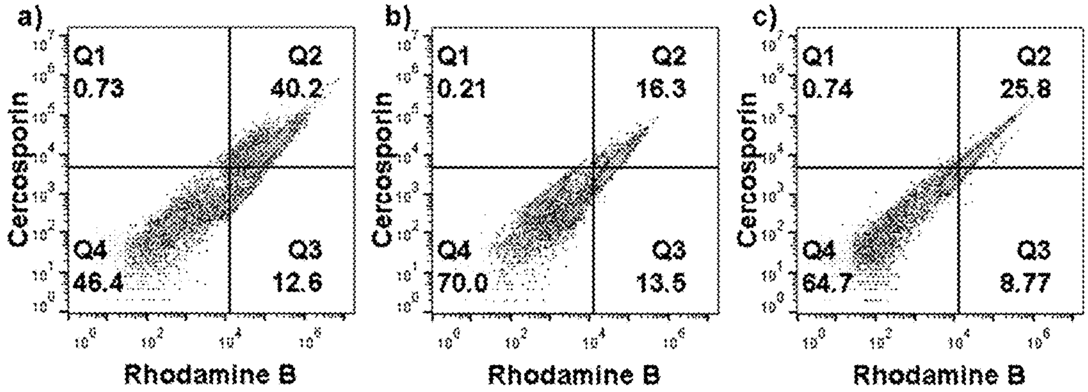
FIG. 7 is flow cytometry results of human hepatoma cells HepG2 and normal HEK293 cells. a) HepG2 cells incubated with photosensitizer multifunctional nanocomposite material Cer@Gal-polymer for 8 hours; b) HEK293 cells incubated with photosensitizer multifunctional nanocomposite material Cer@Gal-polymer for 8 hours; c) experimental results of HepG2 cells incubated with photosensitizer multifunctional nanocomposite material Cer@Gal-polymer for 8 hours under a galactose-containing competition condition.

As shown in FIG. 7, the results show that the amount of Cer@Gal-polymer entering the HEK293 cells is significantly lower than that in HepG2 cells. This is due to low expression of the asialoglycoprotein receptor on the surface of HEK293 cells, so Cer@Gal-polymer cannot rapidly enter the cells by surface galactose-asialoglycoprotein receptor-targeted and mediated endocytosis. In the case where the surface asialoglycoprotein receptor is pre-saturated, Cer@Gal-polymer cannot recognize HepG2 cells via surface-linked galactose, and can only enter tumor cells through non-targeted endocytosis, so the fluorescence intensity of rhodamine B and cercosporin is comparable to that in HEK293 cells. For surface receptor-overexpressed HepG2 cells, Cer@Gal-polymer can rapidly bind with the surface asialoglycoprotein receptors of the tumor cells via surface-linked galactose, and then, enter the tumor cells via receptor-mediated endocytosis, so the fluorescence intensity of both rhodamine B and cercosporin in HepG cells is the highest.

This experiment demonstrates that Cer@Gal-polymer specifically targets and recognizes receptors on the surface of HepG2 cells and is successfully endocytosed into cells.

Example 12

Figure 8:
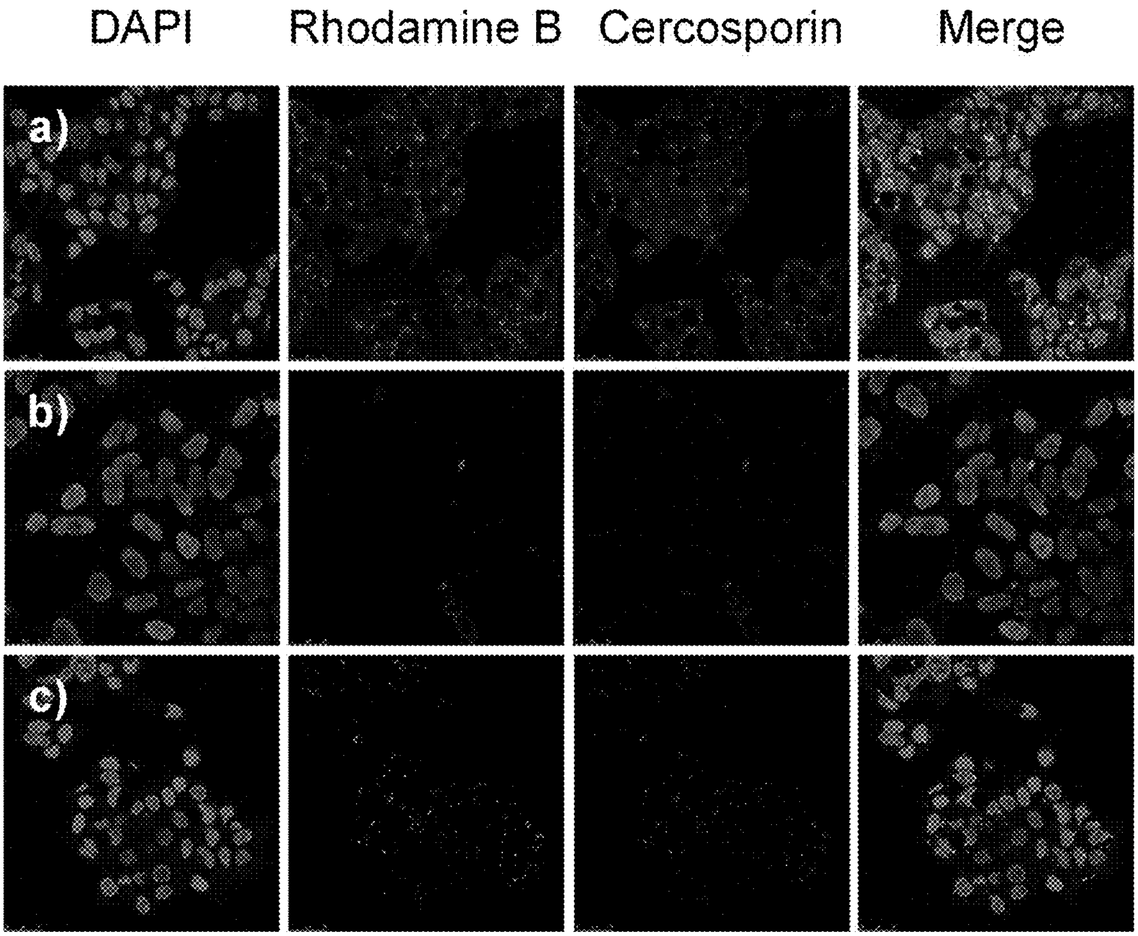
FIG. 8 is results of laser confocal experiments of human hepatoma cells HepG2 and normal HEK293 cells. a) HepG2 cells incubated with photosensitizer multifunctional nanocomposite material Cer@Gal-polymer for 8 hours; b) HEK293 cells incubated with photosensitizer multifunctional nanocomposite material Cer@Gal-polymer for 8 hours; c) Experimental results of HepG2 cells incubated with photosensitizer multifunctional nanocomposite material Cer@Gal-polymer for 8 hours under a galactose-containing competition condition.

Demonstration of Ability of Photosensitizer Multifunctional Nanocomposite Material Cer@Gal-polymer to Specifically Target and Recognize Asialoglycoprotein Receptors on Surface of Hepatoma Cells HepG2 by Laser Confocal Experiments Adding the photosensitizer multifunctional nanocomposite material Cer@Gal-polymer obtained in Example 6 to culture solutions to perform cell culture experiments with HepG2 and HEK293 cells, and then staining the nuclei with 4',6-diamidino-2-phenylindole. It can be seen from the results of laser confocal microscopy experiments in FIG. 8 that fluorescence obviously from rhodamine B in the composite material and fluorescence from cercosporin can be seen in HepG2 cells, but the fluorescence is hardly observed in HEK293 cells; and in the environment with galactose competition, the fluorescence of rhodamine B and cercosporin is also not observed in HepG2 cells. The experiment demonstrates that the photosensitizer multifunctional nanocomposite material Cer@Gal-polymer can recognize and enter HepG2 cells through the galactose-asialoglycoprotein receptor, and cercosporin is released and enters the nucleus.

Example 13

Figure 9:
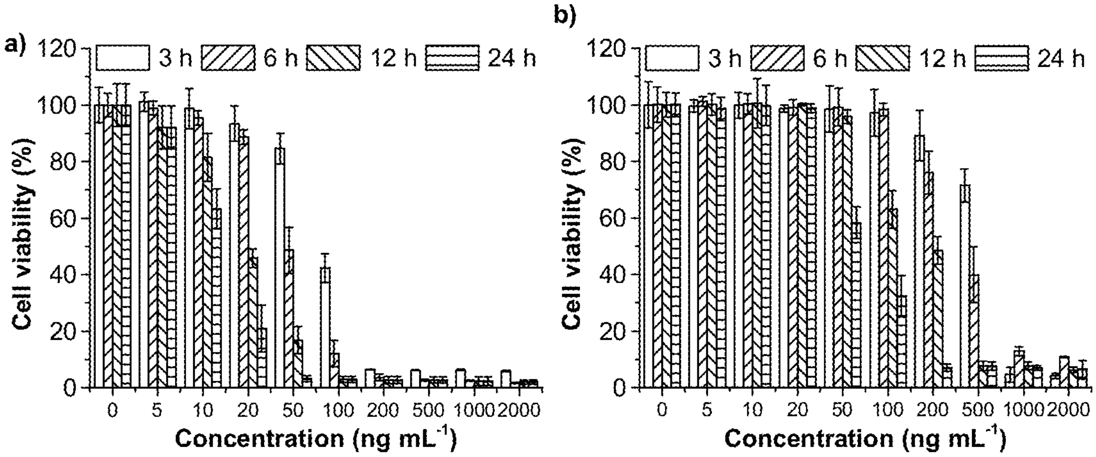
FIG. 9 is cell viability of a) human hepatoma cell HepG2 and b) normal HEK293 cells subjected to 463 nm light irradiation for 15 min after co-culturing with photosensitizer multifunctional nanocomposite material Cer@Gal-polymer for 3, 6, 12 and 24 hours.

Photodynamic Therapy Efficiency of Novel Photosensitizer Multifunctional Nanocomposite Material (Cer@Gal-polymer) at Cell Level Inoculating human hepatoma cells HepG2 cells and normal cells HEK293 cells into 96-well plates and culturing in a 37° C. incubator containing 5% $CO_2$ for 24 hours. After the cells are subjected to adherent growth, adding fresh culture solutions containing different concentrations of Cer@Gal-polymer to continue culturing for 3, 6, 12 or 24 hours. Discarding the culture solutions, washing for three times with PBS of pH 7.4, and adding fresh media. Irradiating the culture dishes with light (463 nm, 20 mW/$cm^2$) for 15 minutes and continuing culturing for 12 hours. Removing the culture solutions again, washing twice with a PBS buffer solution, and adding 100 µL of CCK-8 reagent to each well and continuing culturing for 2 hours in an incubator. Measuring the absorbance (OD) of each well at 450 nm with a multi-functional microplate reader to calculate the cell viability. As shown in FIG. 9, as the incubation time increases, the toxicity of Cer@Gal-polymer to cells increases, and the toxicity of Cer@Gal-polymer to HepG2 is much higher than that to HEK293 cells. By test of the photodynamic therapy toxicity of the Cer@Gal-polymer to human hepatoma cells HepG2 cells and normal cells HEK293 cells, it is demonstrated that Cer@Gal-polymer can targetedly deliver the photosensitizer cercosporin into HepG2 cancer cells through galactose-asialoglycoprotein receptor-mediated endocytosis. At a specific wavelength of 463 nm, Cer@Gal-polymer has a strong phototherapy effect on cancer cells, so the Cer@Gal-polymer exhibits excellent photodynamic therapy performance.

The above-mentioned examples are better examples of the present disclosure, but are not restrictions on the examples of the present disclosure. In this field, any other changes, modifications, combinations, substitutions and simplifications that do not depart from the principles and spirit of the present disclosure belong to the equivalent replacement mode and are included in the scope of protection of the claims of the present disclosure.

What is claimed is:

1. A nanocomposite material comprising a photosensitizer, which comprises a self-assembly of:

a photosensitizer cercosporin, and an acid-sensitive copolymer multifunctional material, wherein the nanocomposite material comprises an ability to target liver tumor cells and is traceable;

wherein the acid-sensitive copolymer multifunctional material has a structural formula shown in formula 1:

Formula 1

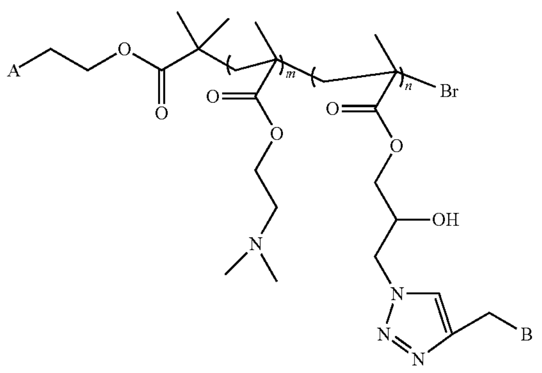

wherein A is one or more identical or different fluorescent molecules having the fluorescent tracing function selected from rhodamine B, fluorescein isothiocyanate and fluoroboron dipyrrole;

wherein B is one or more identical or different monosaccharide or oligosaccharide molecules having galactose or galactosamine residues, which are capable of specifically recognizing over-expressed asialoglycoprotein receptors on the surface of hepatoma cells;

wherein formula 1 comprises the monomer structure of DMAEMA, and m represents the degree of polymerization and is equal to 42; and wherein formula 1 comprises the monomer structure of GMA-$N_3$, and n represents the degree of polymerization and is equal to 62.

2. The nanocomposite material according to claim 1, wherein the acid-sensitive copolymer multifunctional material encapsulates the photosensitizer molecule cercosporin in its hydrophobic cavity by hydrophobic interaction.

3. The nanocomposite material according to claim 1, wherein the loading amount of the cercosporin is about 9% by mass fraction; and wherein the particle size of the multifunctional nanocomposite material is about 103 nm.

4. The nanocomposite material according to claim 1, wherein A is a fluorescent molecule rhodamine B, B is a galactose residue, the molar ratio of the fluorescent molecule rhodamine B to DMAEMA to $GMA-N_3$ is 1:42:62, and the molar ratio of the targeting sugar molecule to $GMA-N_3$ is 1:1.

5. A method for preparing the nanocomposite material of claim 1, comprising:

respectively dissolving the acid-sensitive copolymer multifunctional material and cercosporin in DMSO, and mixing to provide a mixed solution;

dialyzing the mixed solution in double distilled water to prepare a photosensitizer multifunctional nanocomposite material solution;

filtering the photosensitizer multifunctional nanocomposite material solution to remove unloaded cercosporin, and freeze drying the photosensitizer multifunctional nanocomposite material.

6. A method for preparing the nanocomposite material of claim 2, comprising:

respectively dissolving the acid-sensitive copolymer multifunctional material and cercosporin in DMSO, and mixing to provide a mixed solution;

dialyzing the mixed solution in double distilled water to prepare a photosensitizer multifunctional nanocomposite material solution;

filtering the photosensitizer multifunctional nanocomposite material solution to remove unloaded cercosporin, and freeze drying the photosensitizer multifunctional nanocomposite material.

7. The method according to claim 5, wherein the concentration of the acid-sensitive copolymer multifunctional material with liver tumor cell targeting ability and traceability in the dissolving step is 10 mg/mL to 50 mg/mL; wherein the concentration of the cercosporin in the dissolving step is 10 mg/mL to 50 mg/mL; and wherein the amount of the DMSO used in the dissolving step is 0.5 mL to 1 mL.

8. A method for preparing the nanocomposite material of claim 3, comprising:

respectively dissolving the acid-sensitive copolymer multifunctional material and cercosporin in DMSO, and mixing to provide a mixed solution;

dialyzing the mixed solution in double distilled water to prepare a photosensitizer multifunctional nanocomposite material solution;

filtering the photosensitizer multifunctional nanocomposite material solution to remove unloaded cercosporin, and freeze drying the photosensitizer multifunctional nanocomposite material.

9. The method according to claim 8, wherein the concentration of the acid-sensitive copolymer multifunctional material with liver tumor cell targeting ability and traceability in the dissolving step is 10 mg/mL to 50 mg/mL; wherein the concentration of the cercosporin in the dissolving step is 10 mg/mL to 50 mg/mL; and wherein the amount of the DMSO used in the dissolving step is 0.5 mL to 1 mL.

10. A medicine for treating liver cancer, comprising the nanocomposite material of claim 1.

11. A medicine for treating liver cancer, comprising the nanocomposite material of claim 2.

12. A medicine for treating liver cancer, comprising the nanocomposite material of claim 3.

* * * * *